United States Patent [19]
Grollier et al.

[11] Patent Number: 5,643,898
[45] Date of Patent: Jul. 1, 1997

[54] COMBINATION OF DERIVATIVES OF PYRIMIDINE AND OF HYDROCORTISONE FOR INDUCING AND STIMULATING THE GROWTH OF HAIR AND REDUCING ITS LOSS

[75] Inventors: Jean Francois Grollier, Paris; Georges Rosenbaum, Asnières, both of France

[73] Assignee: L'Oreal, Paris, France

[21] Appl. No.: 425,236

[22] Filed: Apr. 18, 1995

Related U.S. Application Data

[63] Continuation of Ser. No. 197,445, Feb. 16, 1994, abandoned, which is a continuation of Ser. No. 288,607, Dec. 22, 1988, abandoned.

[30] Foreign Application Priority Data

Dec. 22, 1987 [LU] Luxembourg .............................. 87.091

[51] Int. Cl.⁶ .......................... A61K 31/56; A61K 31/505
[52] U.S. Cl. .......................... 514/169; 424/70.1; 514/171; 514/256; 514/725; 514/880; 132/207; 132/209
[58] Field of Search ..................... 514/169, 171, 514/256, 725; 132/207, 209, 880, 881; 424/70.1

[56] References Cited

U.S. PATENT DOCUMENTS

| 4,596,812 | 6/1986 | Chidsey | 514/725 |
| 4,684,635 | 8/1987 | Orentreich | 514/171 |
| 5,026,691 | 6/1991 | Kligman | 424/70 |

FOREIGN PATENT DOCUMENTS

| 260010 | 11/1986 | Japan | 424/70 |
| 8505270 | 12/1985 | WIPO | 424/70 |
| WO88/7361 | 10/1988 | WIPO . | |

OTHER PUBLICATIONS

The Merck Index, 1976, pp. 629 & 630.
Patent Abstracts of Japan, vol. 11, No. 115 (C–415)[2562], Apr. 10, 1987 & Japanese Laid–Open Spec. No. 260,010/86, Nov. 18, 1986.
Patent Abstracts of Japan, vol. 11, No. 3 (C–395)[2450], Jan. 7, 1987.
Chemical Abstracts, vol. 106, No. 201544m, STN International.

Primary Examiner—Shelley A. Dodson
Attorney, Agent, or Firm—Jacobson, Price, Holman & Stern, PLLC

[57] ABSTRACT

1. Combination intended to induce and to stimulate the growth of hair and to reduce its loss, characterized in that it comprises:

a) a component (A) containing, in an anhydrous, physiologically acceptable medium, at least hydrocortisone, its salts or esters, and b) a component (B) containing, in en anhydrous, physiologically acceptable medium, at least one pyrimidine derivative corresponding to the formula:

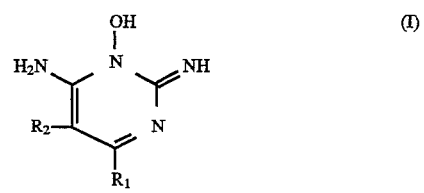

in which $R_1$ denotes a group

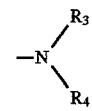

in which $R_3$ and $R_4$, independently of each other, denote hydrogen or an alkyl, alkenyl, alkylaryl or cycloalkyl group; $R_3$ and $R_4$ may also form a heterocyclic ring with the nitrogen atom to which they are linked, which is chosen from aziridinyl, azetidinyl, pyrrolidinyl, piperidyl, hexahydroazepinyl, heptamethyleneimine, actamethyleneimine, morphaline and 4-(lower) aklylpiperazidinyl groups, it being possible for the heterocyclic groups to be substituted on the carbon atoms by one to three lower alkyl, hydroxyl or alkoxy groups; the group $R_2$ is chosen from a hydrogen atom and an alkyl, alkenyl, alkylalkoxy, cycloalkyl, aryl, alkylaryl, arylalkyl, alkylarylalkyl, alkoxyarylalkyl or haloarylalkyl group, and the addition salts of physiologically acceptable acids, the components (A) and (B) forming part of a same single composition or being intended to be employed separately, either simultaneously or successively or after an interval of time, on the scalp or the hair.

10 Claims, No Drawings

COMBINATION OF DERIVATIVES OF PYRIMIDINE AND OF HYDROCORTISONE FOR INDUCING AND STIMULATING THE GROWTH OF HAIR AND REDUCING ITS LOSS

This application is a continuation of application Ser. No. 08/197,445, filed Feb. 16, 1994, abandoned, which is a continuation of application Ser. No. 07/288,607, filed Dec. 22, 1988, abandoned.

The invention relates to the combination of derivatives of pyrimidine and of hydrocortisone with a view to inducing and stimulating the growth of hair and reducing its loss.

The activity of hair follicles is cyclic. The anagen phase, which lasts several years and during which the hair lengthens, is followed by a phase of rest (telogen) of a few months. During this period of rest the hair falls out and another cycle begins again.

The head of hair is thus continually renewed; out of the 100,000 to 150,000 hairs which make up a head of hair, at any time approximately 10% are at rest and will therefore be replaced in a few months.

In almost all cases, the loss of hair appears in individuals who are genetically susceptible; more particularly, it affects men.

This alopecia is a disorder of the renewal of hair which, in a first stage, entails an acceleration of the cycle frequency at the expense of the quality of hair, and then of its quantity. There is a progressive depletion of hair due to regression of a part of so-called "terminal" hair at the "down" stage. Regions are affected preferentially: temporal-frontal bays in men; diffuse alopecia of the crown in women.

Among the alopecias, the acquired, noncicatricial and diffuse alopecias, such as androgenetic or androgenic alopecia, are particularly difficult to treat, in contrast to localized alopecias such as pelade which would appear to be immunological in origin.

Topical treatment of pelade with fluorinated corticosteroids such as fluocinolone, halcinonide and dexamethasone have already been proposed in the past. On the other hand, until now, their use in the field of the treatment of androgenetic alopecia has not been found satisfactory.

Compounds such as 6-amino-1,2-dihydro-1-hydroxy-2-imino-4-piperidinopyrimidine or minoxidil have also been employed, furthermore, in compositions making it possible to reduce or to eliminate the effect of alopecia and to induce and to stimulate the growth of hair and to reduce its loss.

The Applicant has now found that combining hydrocortisone with certain pyrimidine derivatives in anhydrous medium resulted surprisingly in the finding of an improved induction and stimulation of the growth of hair and a more powerful action on the retardation of hair loss, particularly in the case of diffuse alopecias.

This effectiveness is characterized in particular by a superior activity when compared with the pyrimidine derivatives employed by themselves or compared with steroidal antiinflammatory agents.

The Applicant has also found that the combination in accordance with the invention made it possible to obtain a faster effect than in the past, or to employ the pyrimidine derivative at a lower concentration, In order to determine the effectiveness or the speed of action of the alopecia compositions, use is generally made of the trichogram, and more particularly the phototrichogram which makes it possible to determine, inter alia, the percentage of hair in an anagen phase, relative to hair in a telogen phase.

The invention thus essentially seeks to increase the ratio of the number of hairs in an anagen phase relative to the number of hairs in a telogen phase.

A subject of the invention consists, therefore, of the combination of hydrocortisone with pyrimidine derivatives in an anhydrous medium, with a view to inducing or stimulating the growth of hair and reducing its loss.

Another subject of the invention consists of an anhydrous cosmetic or pharmaceutical composition containing this combination.

A further subject of the invention is a device with a number of compartments or "kits", or an outfit incorporating the combination.

Other subjects of the invention will become apparent on reading the description and the examples which follow.

The combination in accordance with the invention is essentially characterized in that it consists of:
a) a component (A) comprising, in an anhydrous, physiologically acceptable medium, at least hydrocortisone or its salts and esters,
b) a component (B) containing, in a physiologically anhydrous acceptable medium, at least one pyrimidine derivative corresponding to the formula:

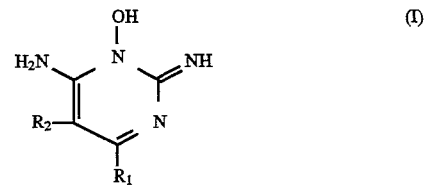

in which $R_1$ denotes a group

in which $R_3$ and $R_4$, independently of each other, denote hydrogen or an alkyl, alkenyl, alkylaryl or cycloalkyl group; $R_3$ and $R_4$ may also form a heterocyclic ring with the nitrogen atom to which they are linked, which is chosen from aziridinyl, azetidinyl, pyrrolidinyl, piperidyl, hexahydroazepinyl, heptamethyleneimine, octamethyleneimine, morpholine and 4-(lower) alkylpiperazidinyl groups, it being possible for the heterocyclic groups to be substituted on the carbon atoms by one to three lower alkyl, hydroxyl or alkoxy groups; the group $R_2$ is chosen from a hydrogen atom and an alkyl, alkenyl, alkylalkoxy, cycloalkyl, aryl, alkylaryl, arylalkyl, alkylarylalkyl, alkoxyarylalkyl or haloarylalkyl group, and the addition salts of physiologically acceptable acids, the components (A) and (B) forming part of the same single composition or being intended to be employed separately, either simultaneously or successively or after an interval of time with a view to inducing and stimulating the growth of hair and reducing its loss.

The hydrocortisone salts and esters are chosen in particular from the 21-acetate, the 21-bendazac, the 17-valerate, the 17-butyrate, the 21-cyclopentylpropionate, the 21-hemisuccinate, the hexanoate, the disodium 21-phosphate, the sodium 21-succinate and the tert-butylacetate.

Hydrocortisone and hydrocortisone 21-acetate are particularly preferred.

In the case of the compounds of formula (I), the alkyl or alkoxy group preferably denotes a group containing 1 to 4 carbon atoms; the alkenyl group preferably denotes a group containing 2 to 5 carbon atoms; the aryl group preferably denotes a phenyl group, and the cycloalkyl group preferably denotes a group containing 4 to 6 carbon atoms.

The groups of formula (I) which are particularly preferred are chosen from the compounds in which $R_2$ denotes hydrogen, and $R_1$ denotes a group:

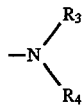

in which $R_3$ and $R_4$ form a piperidyl ring, and their salts such as, for example, the sulphate.

A particularly preferred compound among these compounds consists of 6-amino-1,2-dihydro-1-hydroxy-2-imino-4-piperidinopyrimidine, also known as minoxidil.

Hydrocortisone or its salts or esters are employed in component (A) in proportions of between 0.0 and 5% by weight, preferably between 0.2 and 3%, and more particularly between 0.2 and 1% by weight; the pyrimidine derivative of formula (I) is preferably employed in component (B) in proportions of between 0.05 and 10% by weight, preferably between 0.05 and 5% by weight and in particular between 0.5 and 4% by weight.

When the components (A) and (B) are employed a single composition, the proportion of hydrocortisone, its salts or esters is between 0.01 and 3% by weight relative to the total weight of the composition, preferably between 0.01 and 2% and in particular between 0.01 and 1%, and the pyrimidine derivative of formula (1) is employed in proportions of between 0.05 and 6% by weight relative to the total weight of the composition, preferably between 0.1 and 5% and in particular between 0.5 and 3% by weight.

The physiologically acceptable medium for the components (A) and (B) is an anhydrous medium which may be employed in pharmacy and in cosmetics and may consist particularly of a solvent or a mixture of cosmetically or pharmaceutically acceptable organic solvents.

The solvents which may be employed are more particularly chosen from $C_1$–$C_4$ lower alcohols such as ethyl alcohol, isopropyl alcohol, tert-butyl alcohol, alkylene glycols such as propylene glycol, mono- and dialkylene glycol alkyl ethers, and more particularly ethylene glycol monoethyl ether, propylene glycol monomethyl ether and diethylene glycol monoethyl ether.

A medium containing less than 1% of water is called an anhydrous medium.

The physiologically acceptable medium may be thickened or not. Thickening or gelling agents which are well known in the state of the art are employed for this purpose, such as, more particularly, heterobiopoly-saccharides like xanthan gum or scleroglucans, cellulose derivatives, and crosslinked or uncrosslinked acrylic polymers.

The thickeners are preferably present in proportions of between 0.1 and 5% by weight and in particular between 0.4 and 3% by weight relative to the total weight of each of the components when they are employed separately or relative to the total weight of the composition containing the components (A) and (B).

The compositions consisting either of the components (A) and (B) or of the composition containing both components (A) and (B) may also contain any other adjuvants which are usually employed in compositions intended for a topical, cosmetic or pharmaceutical application, and more particularly preserving agents, complexing agents, colorants, alkalifying or acidifying agents, anionic, cationic, nonionic or amphomeric surface-active agents or mixtures thereof, and anionic, cationic, nonionic or amphoteric polymers, as well as mixtures thereof.

These compositions may also be packaged under pressure in aerosol devices.

In component (B), the pyrimidine derivatives of formula (I) may be present either in dissolved form in the physiologically acceptable medium or else totally or partially suspended in this medium, in particular in the form of particles which have a particle size of less than 80 microns, preferably less than 20 microns and in particular less than 5 microns.

A first embodiment of the invention consists in employing the combination defined above in the form of a composition containing the components (A) and (B).

A particularly preferred form of the invention consists in storing the components (A) and (B) in separate devices and preparing the composition containing hydrocortisone, its salts or esters and the pyrimidine derivative of formula (I) extemporaneously just before application.

Lastly, another embodiment consists in applying the components (A) and (B) separately, either simultaneously or successively or after an interval of time.

In these cases, the combination in accordance with the invention may be packaged, in particular, in a multicompartment device also known as a kit or outfit; the first compartment containing the component (A) with the hydrocortisone, its salts or esters, and the second compartment contains the component (B) based on the pyrimidine derivative of formula (I). This device may be provided with a means of mixing the compositions just at the time of application.

The treatment for inducing and stimulating the growth of hair and reducing its loss consists chiefly in applying the combination such as defined above to the alopecic regions of the scalp and of the hair of a person, either by means of a single composition, or by application of the components (A) and (B) or (B) and (A), successively or after an interval of time.

The preferred method of application consists in applying 1 to 2 grams of the composition or of each of the components (A) and (B) to the alopecic region of the scalp at a frequency of one to two applications daily for 1 to 7 days per week, this being done for a period of 1 to 6 months.

The Applicant has found particularly significant effects at the end of two months' treatment.

The treatment process exhibits the characteristics of a therapeutic treatment insofar as the combination in accordance with the invention has a therapeutic activity on the biological mechanisms of the pilary cycle and on disorders thereof.

Another subject of the invention is therefore the use of a combination such as defined above for the preparation of a medication the effect of which is to induce or to stimulate the growth of hair and to retard its loss.

Furthermore, the process exhibits the characteristics of a cosmetic process, insofar as it allows the hair or the scalp to be made more attractive, within the cosmetic meaning of the term.

The following examples are intended to illustrate the invention without, however, being limiting in nature.

EXAMPLE 1

The following composition is prepared:
Minoxidil 0.625 g
Hydrocortisone 0.625 g

Distilled propylene glycol 6.45 g
Absolute ethyl alcohol q.s. 100.00 g

This lotion is applied to the alopecic regions of the scalp daily during a period of treatment of 3 months; each month an effect of regrowth of hair is ascertained as an increase in its overall density and in the density of the hair in anagen phase.

EXAMPLE 2

The following composition is prepared:
Minoxidil 2.5 g
Hydrocortisone 0.625 g
Distilled propylene glycol 6.45 g
Absolute ethyl alcohol q.s. 100.00 g

EXAMPLE 3

Two compositions (A) and (B) are packaged as a kit containing, respectively:
Composition (A)
Hydrocortisone 2.00 g
Distilled propylene glycol 6.45 g
Absolute ethyl alcohol q.s. 100.00 g
Composition (B):
Minoxidil 2.5 g
Distilled propylene glycol 6.45 g
Absolute ethyl alcohol q.s. 100.00 g

EXAMPLE 4

Minoxidil 2.00 g
Hydrocortisone 21-acetate 0.30 g
Distilled propylene glycol 6.45 g
Absolute ethyl alcohol q.s. 100.00 g

EXAMPLE 5

Minoxidil 1.5 g
Hydrocortisone 21-acetate 0.45 g
Propylene glycol monomethyl ether 50.00 g
Absolute ethyl alcohol q.s. 100.00 g

EXAMPLE 6

Two compositions (A) and (B) are packaged as a kit containing, respectively:
Composition (A):
Hydrocortisone 21-hemisuccinate 0.3 g
Absolute ethyl alcohol q.s, 100.00 g
Composition (B):
Minoxidil 2.5 g
Distilled propylene glycol 6.45 g
Absolute ethyl alcohol q.s, 100.00 g (A) and then (B) are applied in immediate succession to the alopecic regions of the scalp, 75% by weight of composition (A) being mixed with 75% by weight of composition (B) before the application.

We claim:

1. A combination of components that is effective for use in inducing and stimulating hair growth and for decreasing hair loss, said combination comprising:

(a) a first component (A), comprising in an anhydrous, physiologically acceptable medium an effective amount of at least hydrocortisone, its salts or esters; and (b) a second component (B), comprising a physiologically acceptable medium and an effective amount of at least one pyrimidine derivative having the formula:

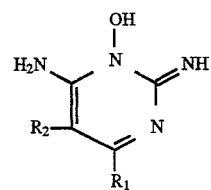

as well as acid addition salts thereof, wherein $R_1$ represents a group having the formula:

wherein $R_3$ and $R_4$ are selected from the group consisting of hydrogen, lower alkyl, alkenyl, alkylaryl and cycloalkyl, the alkyl part of which is a lower alkyl radical, or $R_3$ and $R_4$, with the nitrogen to which they are each bound, form a heterocyclic group, which is unsubstituted or is substituted on the carbon atoms with one to three lower alkyl, hydroxy, or alkoxy, and which is selected from the group consisting of aziridinyl, azetidinyl, pyrrolidinyl, piperidino, hexahydrolazepinyl, heptamethylenimino, octamethyleneimino, morpholino and 4-(lower alkyl) piperazinyl, and wherein $R_2$ is selected from the group consisting of hydrogen, lower alkyl, alkenyl, alkoxyalkyl, cycloalkyl, aryl, alkylaryl, arylalkyl, alkylarylalkyl, alkoxyarylalkyl and haloarylalkyl, the alkyl part of which is a lower alkyl radical, wherein said components are used as separate components that are used either successively or intermittently or are mixed immediately prior to use for use as a composition containing said components and wherein said effective amount of each component is effective, when used as a combination, to induce and stimulate hair growth and reduce its loss.

2. The combination of claim 1, wherein said hydrocortisone salts or esters are selected from the group of hydrocortisone salts or esters consisting of the 21-acetate, the 21-bendazac, the 17-valerate, the 17-butyrate, the 21-cyclopentylpropionate, the 21-hemisuccinate, the hexanoate, the disodium 21-phosphate, the sodium 21-succinate and the tert-butylacetate.

3. The combination of claim 1, wherein said pyrimidine derivative of formula (I) is 6-amino-1,2-dihydro-1-hydroxy-2-imino-4-piperidinopyrimidine or minoxidil.

4. The combination of claim 1, wherein said hydrocortisone, its salts or esters are present in component (A) at a concentration of between 0.01 and 5% by weight, and wherein said pyrimidine derivative is present in component (B) at a concentration of between 0.05 and 10% by weight.

5. The combination of claim 1, wherein the combination is mixed immediately prior to use to form a single composition and wherein the concentration of said hydrocortisone, its salts or esters in said composition is between 0.01 and 3% by weight relative to the total weight of the composition and the concentration of said pyrimidine derivative of formula (I) is between 0.05 and 6% by weight relative to the total weight of the composition.

6. The combination of claim 1, wherein said anhydrous, physiologically acceptable medium for components (A) and (B) contains a mixture of cosmetically or pharmaceutically acceptable organic solvents selected from the group consisting of $C_1$–$C_4$ lower alcohols, alkylene glycols and mono-and dialkylene glycol alkyl ethers.

7. The combination of claim 1, wherein at least one of the components (A) and (B) is thickened by means of thickening agents or gelling agents.

8. The combination of claim 1, wherein at least one of the components (A) and (B) also contains cosmetically or pharmaceutically acceptable adjuvants selected from the group consisting of preserving agents, complexing agents, colorants, alkalifying agents, acidifying agents, anionic surface-active agents, nonionic surface-active agents, amphoteric surface-active agents, mixtures of anionic surface-active agents, nonionic surface-active agents, and amphoteric surface-active agents, anionic polymers, cationic polymers, amphoteric polymers and mixtures of anionic polymers, cationic polymers and amphoteric polymers.

9. A method for the treatment of androgenetic alopecia, comprising: applying an effective amount of the combination of claim 1 to the scalp or hair either successively, intermittently or as a single composition that is mixed immediately prior to use, wherein said amount is effective for inducing and stimulating hair growth and reducing its loss.

10. A multicompartment device or kit, comprising at least two compartments wherein one of said compartments contains component (A) of the combination of claim 1 and another of said compartments contains component (B) of the combination of claim 1.

* * * * *